US00PP36439P2

(12) United States Plant Patent
Ohde

(10) Patent No.: US PP36,439 P2
(45) Date of Patent: Feb. 11, 2025

(54) ***LIPPIA NODIFLORA* PLANT NAMED 'ECOLOPIA 4'**

(50) Latin Name: *Lippia nodiflora*
Varietal Denomination: ECOLOPIA 4

(71) Applicant: Masataka Ohde, Oyama (JP)

(72) Inventor: Masataka Ohde, Oyama (JP)

( * ) Notice: Subject to any disclaimer, the term of this patent is extended or adjusted under 35 U.S.C. 154(b) by 0 days.

(21) Appl. No.: 18/888,186

(22) Filed: Sep. 18, 2024

(51) Int. Cl.
*A01H 5/02* (2018.01)
*A01H 6/86* (2018.01)

(52) U.S. Cl.
USPC ..... Plt./263.1
CPC ..... *A01H 6/86* (2018.05)

(58) Field of Classification Search
USPC ..... Plt./263.1
CPC ..... A01H 5/02
See application file for complete search history.

*Primary Examiner* — Kent L Bell

(57) ABSTRACT

A new and distinct cultivar of *Lippia* plant named 'ECOLOPIA 4' is disclosed, characterized by uniquely long internodes, about 2.6 cm, resulting in tall plants. Plants of the new variety grow vigorously to about 160 cm wide in 3 months and 2 cm tall. The new variety has excellent tolerance for heat, humidity and disease. Foliage is larger than average, plants are sterile. The new variety is a *Lippia*, useful for a variety of horticultural purposes.

7 Drawing Sheets

Latin name of the genus and species: *Lippia nodiflora*.
Variety denomination: 'ECOLOPIA 4'.

BACKGROUND OF THE INVENTION

The new *Lippia* cultivar is a product of chance discovery by the inventor, Masataka Ohde, in Oyama, Japan. The new variety was discovered as a naturally occurring single plant mutation in a greenhouse in Oyama, Japan.

The parent is an unnamed, unpatented variety of *Lippia nodiflora*. The new variety was discovered June 2021 by the inventor in a group of plants of the parent variety.

Asexual reproduction of the new cultivar 'ECOLOPIA 4' was first performed at a commercial greenhouse in Oyama, Japan by terminal vegetative cuttings during July 2021. More than 3 generations have been reproduced by vegetative cuttings. Subsequently, propagation has also shown that the unique features of this cultivar are stable and reproduced true to type.

SUMMARY OF THE INVENTION

The cultivar 'ECOLOPIA 4' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ECOLOPIA 4'. These characteristics in combination distinguish 'ECOLOPIA 4' as a new and distinct *Lippia* cultivar:

1. Long internode of about 2.6 cm.
2. Tolerance to disease.
3. Tolerance to high humidity.
4. Above average foliage size.

5. Variety is sterile.
6. Rapid growth.

PARENT COMPARISON

Plants of the new cultivar 'ECOLOPIA 4' are similar to the parent variety in most horticultural characteristics. The new variety however differs in the following characteristics:

1. Internodes of the new variety average 2.6 cm, internodes of the parent average 1.6 cm.
2. The new variety is faster growing than the parent variety.
3. Leaf length of the new variety is about 1.7 cm, leaf length of the parent is about 1.1cm.
4. Peduncles of the new variety are about 4 cm; peduncles of the parent are about 2.1 cm.
5. Leaf width of the new variety is about 0.9 cm, leaf width of the parent is about 0.8 cm.

COMMERCIAL COMPARISON

Plants of the new cultivar 'ECOLOPIA 4' are similar to the commercial variety *Lippia* 'Campagna Verde' U.S. Plant Pat. No. 20,120 in most horticultural characteristics. The new variety however differs in the following characteristics:

1. Shorter plant height, measured at foliar plane. 'Campagna Verde' grows to 3 cm, the new variety grows to 2 cm.
2. Stronger tolerance to disease under high heat and high humidity conditions.
3. Corolla color of 'Campagna Verde' is Violet-Blue 91D, corolla color of 'ECOLOPIA 4' is RHS Purple 75B.

'ECOLOPIA 4' can be compared to the commercial variety *Lippia nodiflora* 'ECOLOPIA1' U.S. Plant Pat. No. 27,036. Plants of 'ECOLOPIA1' are similar to plants of 'ECOLOPIA 4' in most horticultural characteristics. However, 'ECOLOPIA 4' differs from 'ECOLOPIA1' in the following characteristics:

1. Internodes of the new variety average 2.6 cm, internodes of 'ECOLOPIA1' average 1.7 cm.

2. Leaf length of the new variety is about 1.7 cm, leaf length of 'ECOLOPIA1' is about 1 cm.
3. Peduncles of the new variety are about 4 cm, peduncles of 'ECOLOPIA1' are about 2.5 cm.
4. Fully opened Corolla color of 'ECOLOPIA1' is RHS Violet-Blue 91D, corolla color of 'ECOLOPIA 4' is RHS Purple 75B.

BRIEF DESCRIPTION OF THE PHOTOGRAPHS

The accompanying photograph in FIG. 1 illustrates in full color a close-up view of typical flowers and foliage of a plant of 'ECOLOPIA 4' grown outdoors in Oyama, Japan.

Figure 1:
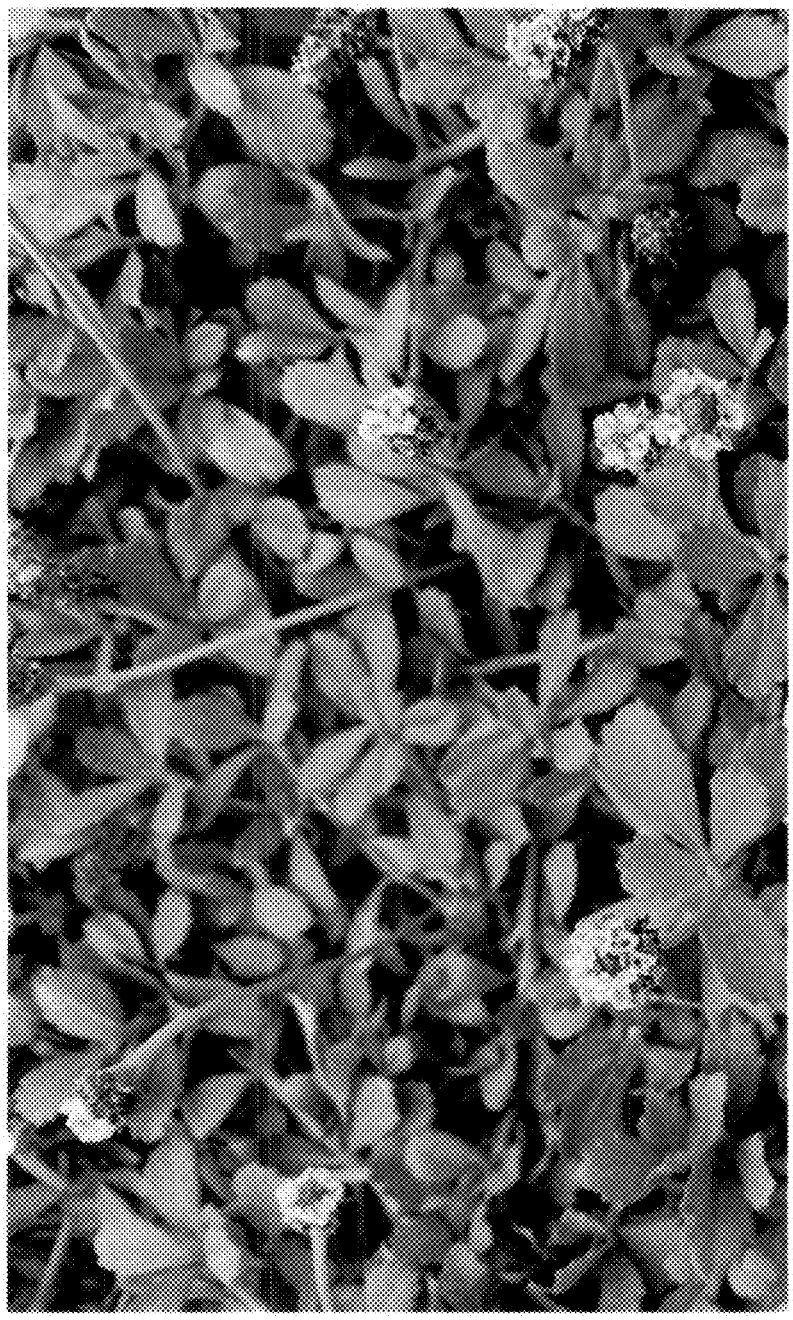
Figure 2:
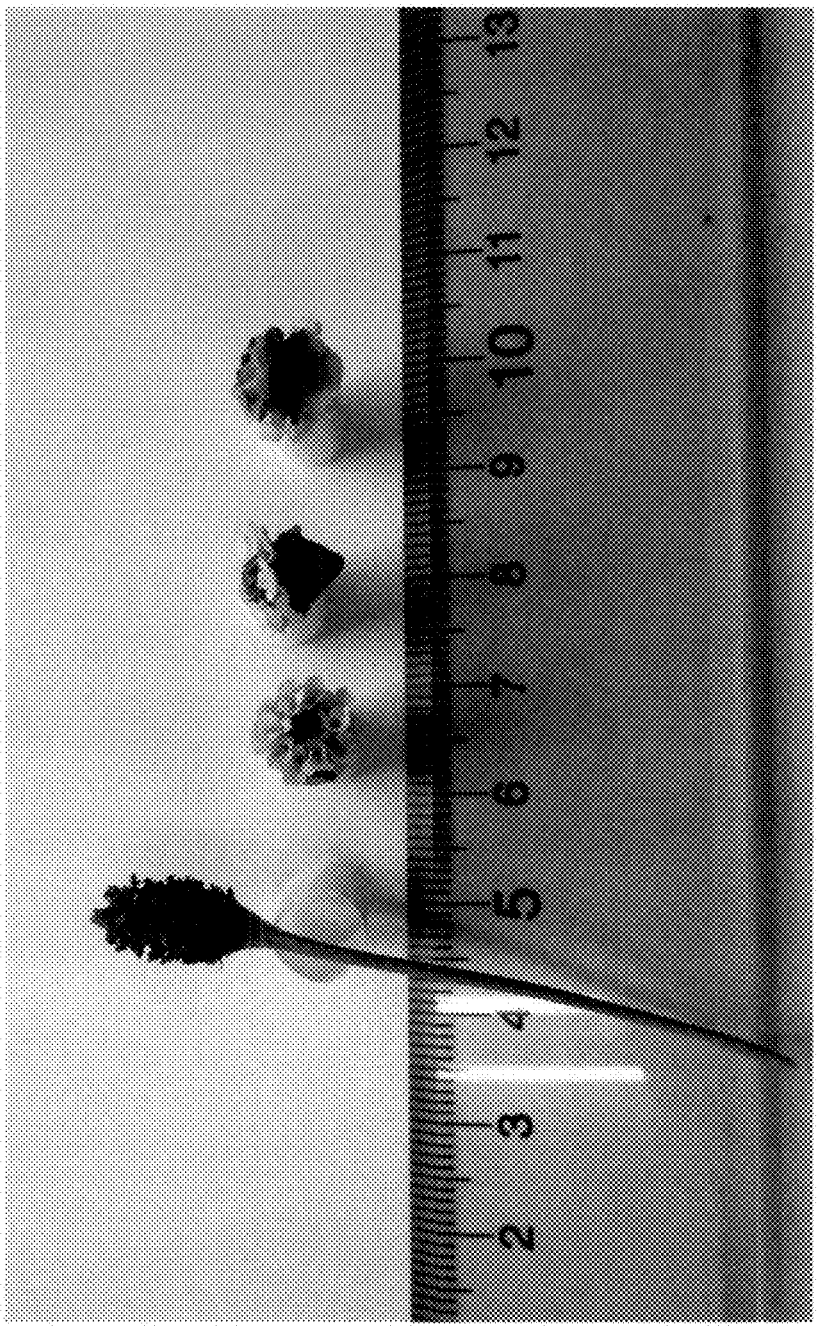
FIG. 2 illustrates a close-up view of a typical inflorescence, with a centimeter ruler for scale.
Figure 3:
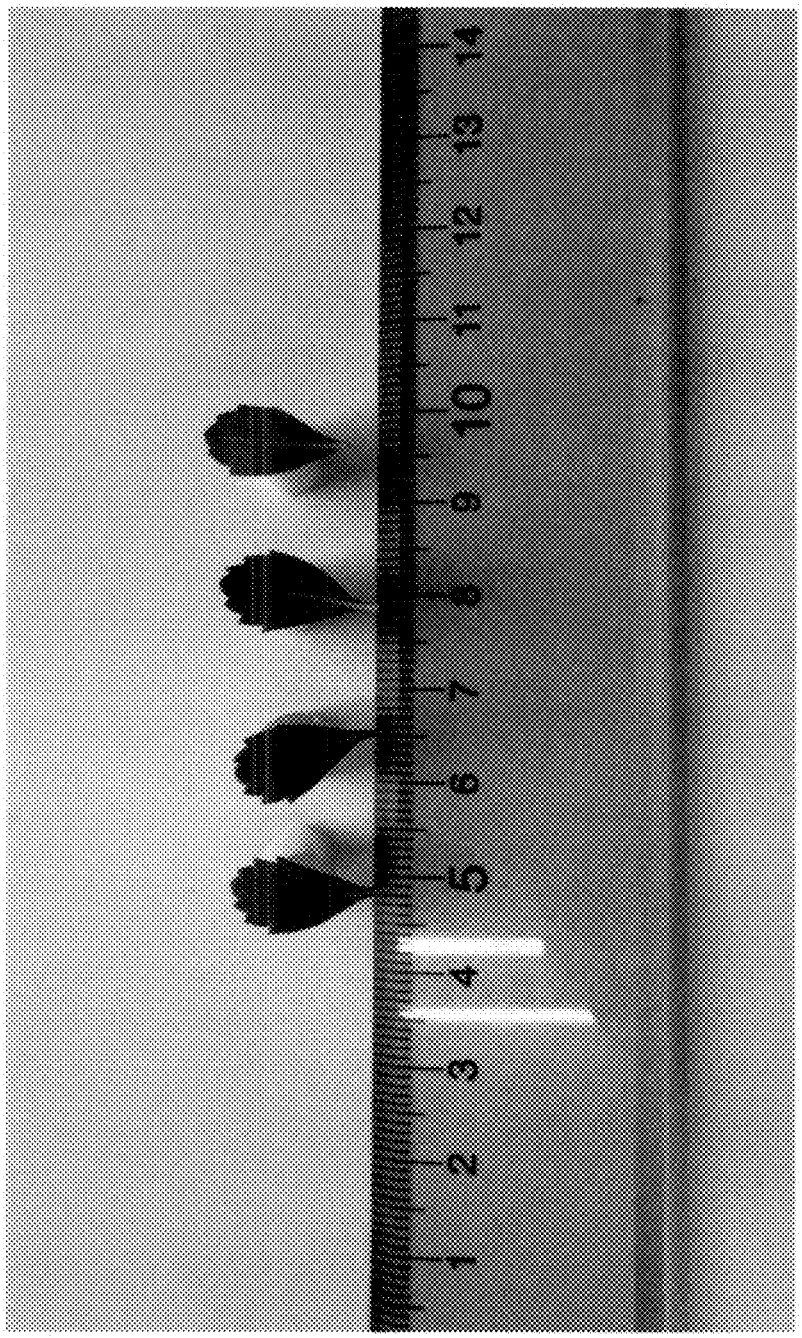
FIG. 3 illustrates a close-up view of foliage, with a centimeter ruler for scale.
Figure 4:
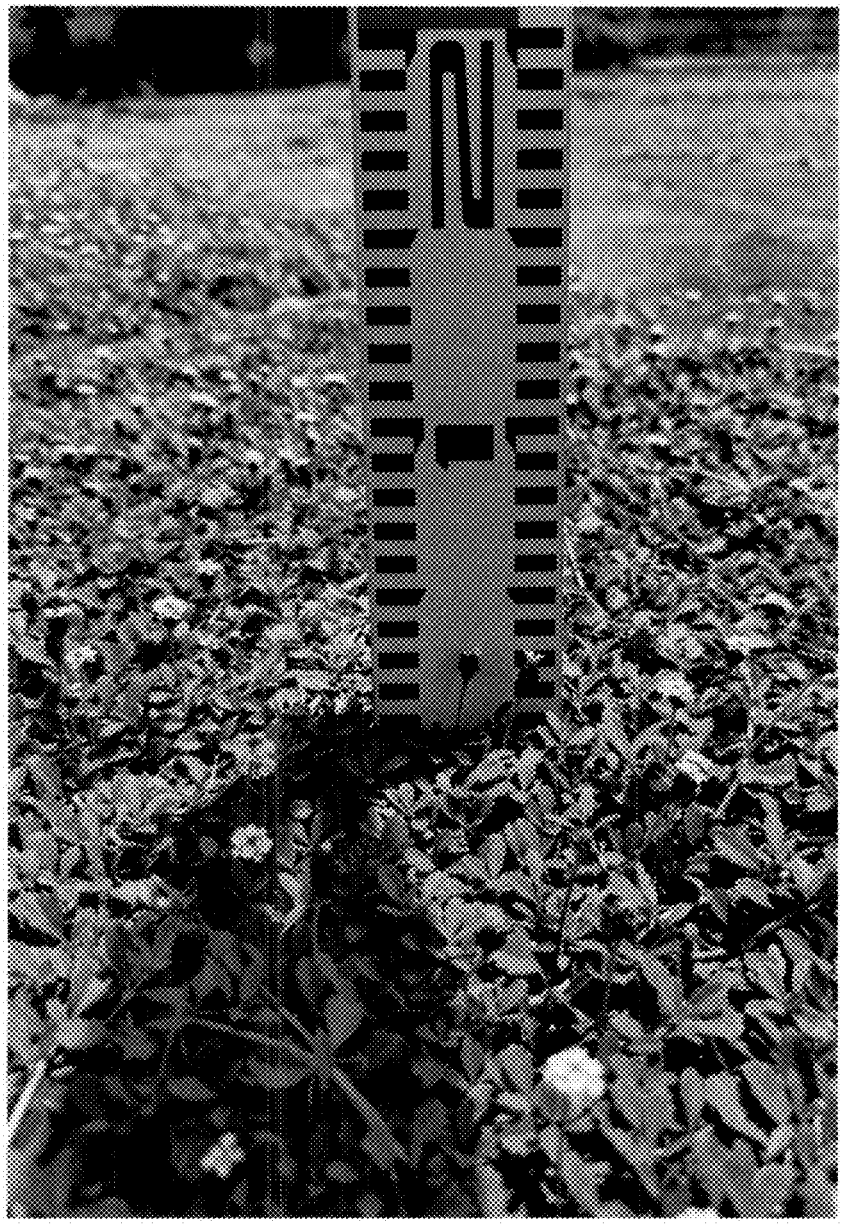
FIG. 4 illustrates a mass planting view of the plant grown outdoors.
Figure 5:
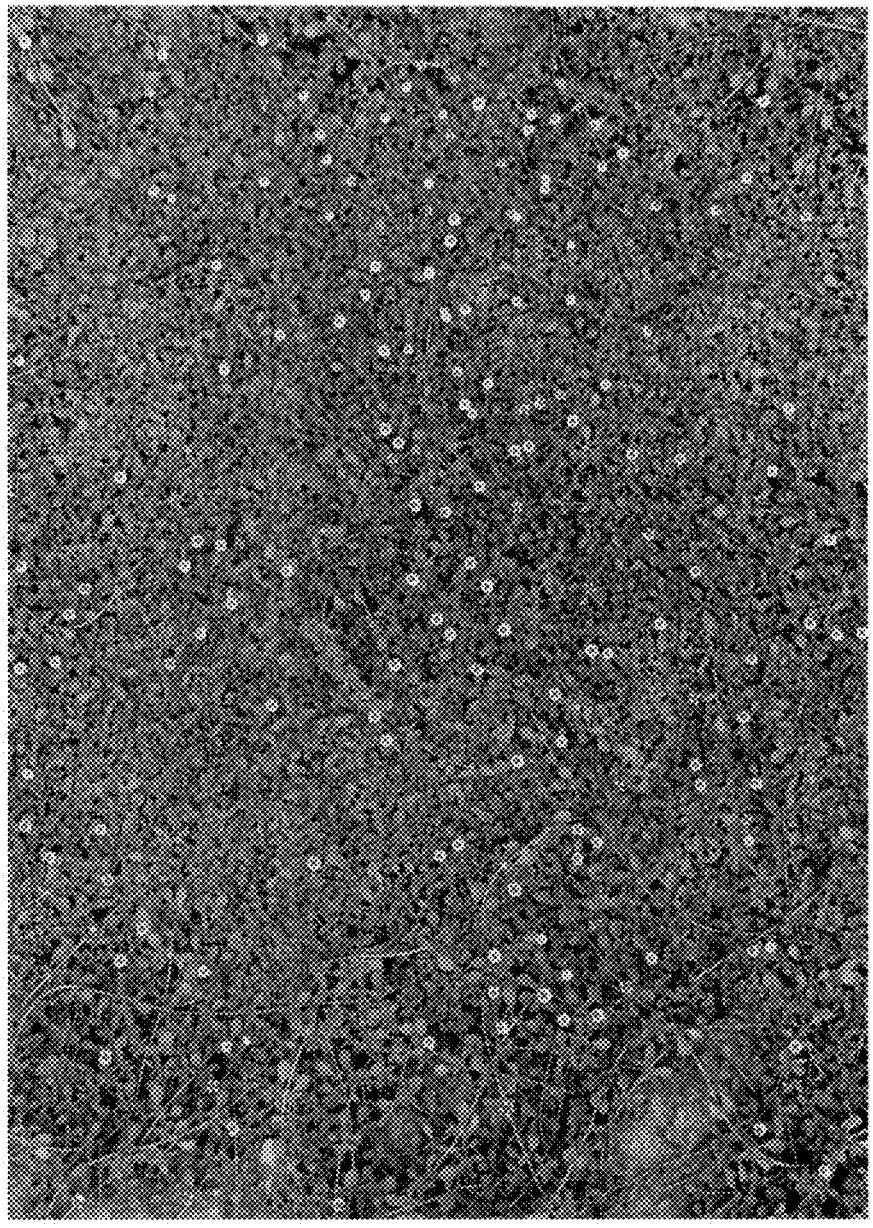
FIG. 5 shows field grown plants of the new variety.
Figure 6:
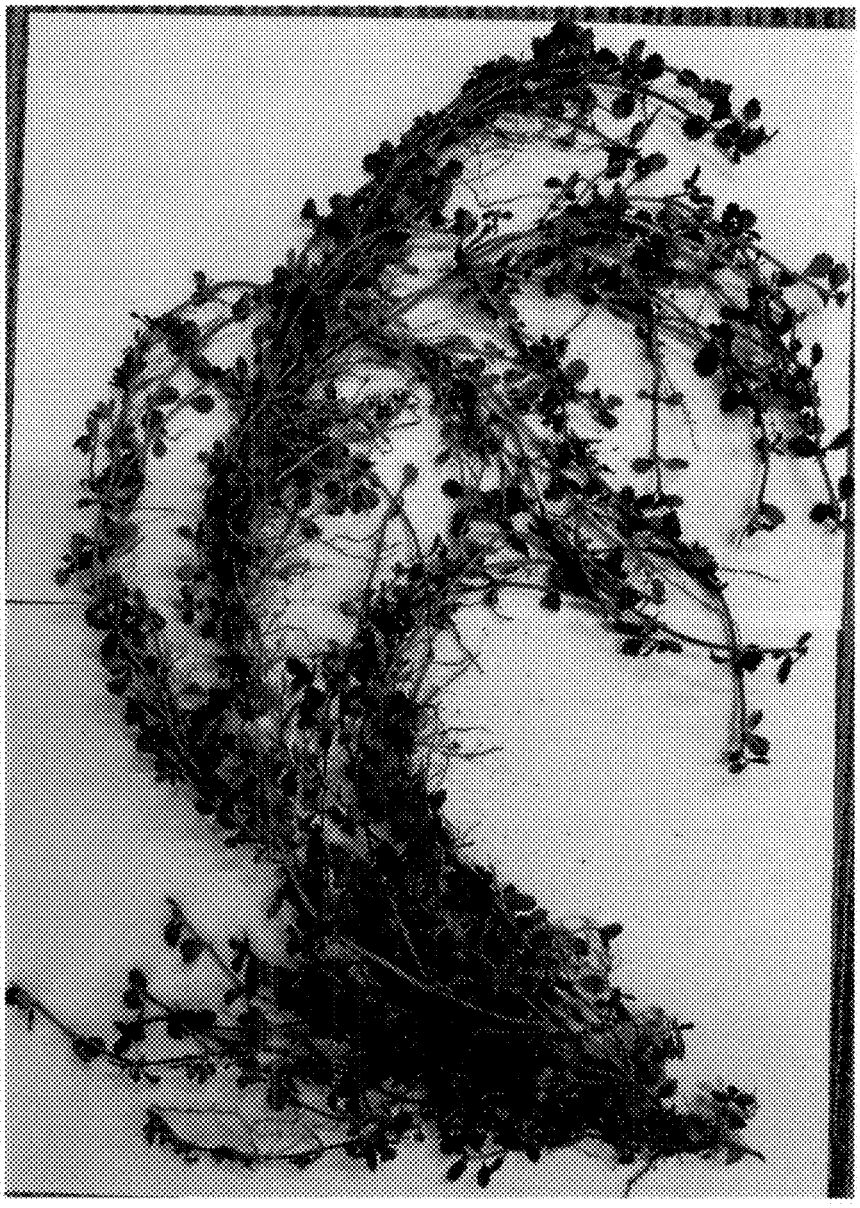
FIG. 6 illustrates a piece of the 3 months old plant, with nodes rooting.
Figure 7:
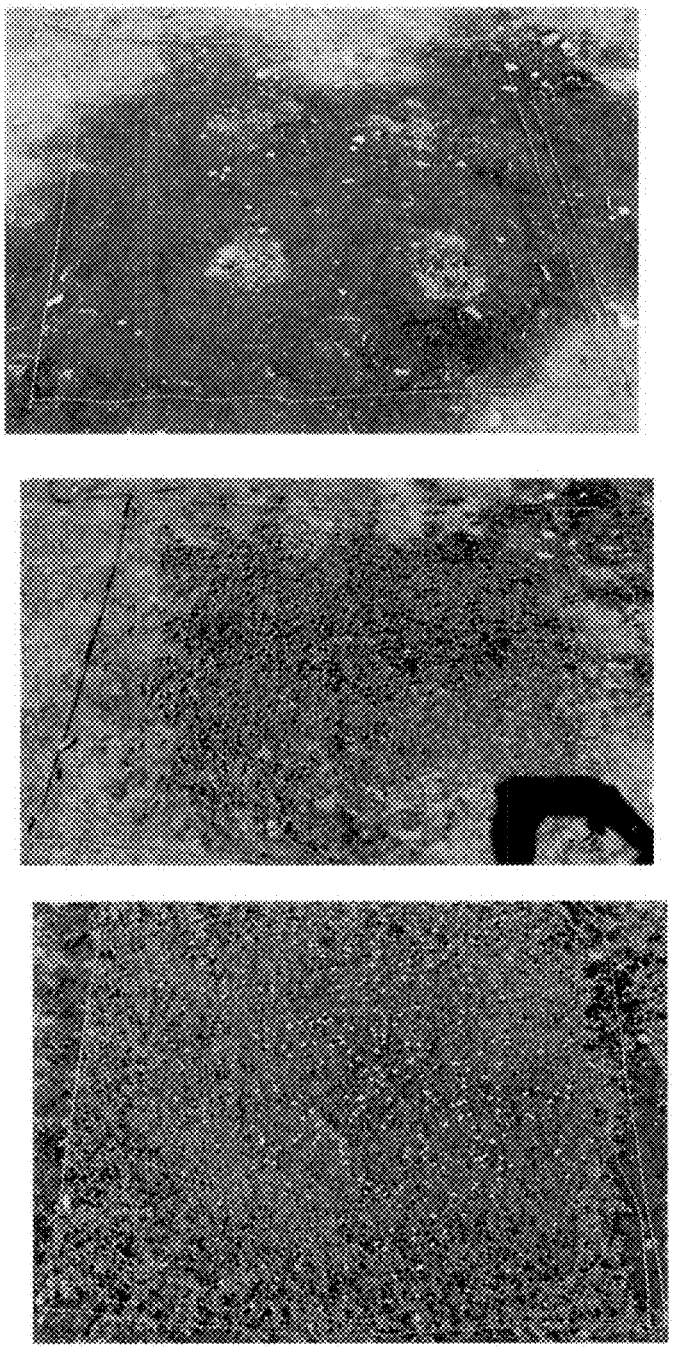
FIG. 7 illustrates plants of 'ECOLOPIA 4' at 3 different stages. Plants on the top of the figure have just been planted, plants in the center of 30 days old, plants on the bottom of the figure are 3 months old.

The photographs were taken using conventional techniques and although colors may appear different from actual colors due to light reflectance it is as accurate as possible by conventional photographic techniques.

DETAILED BOTANICAL DESCRIPTION

General growing conditions of plant described: The following botanical description of 'EPOLOPIA 4' describes asexually reproduced plants of the new cultivar 'ECOLOPIA 4' grown in both an outside research field with plowed soil supplemented with fertilizer containing 8% N, 8% P, and 8% K, and in temperature-controlled and uncontrolled greenhouses in a mixture of Kanuma soil, peat and vermiculite supplemented with the same fertilizer. Plants were grown in Oyama, Tochigi, Japan and measured in August of 2024. Averages have been taken from various plants in these different conditions. Temperatures ranged from 3° C. to 50° C. during the day and from −5° C. to 30° C. at night. Age of the plants described is approximately 90 days from a rooted cutting. Color references are from The R.H.S. Colour Chart 2015.

PROPAGATION

Typical propagation method: Herbaceous cutting.
Time to initiate roots: 3 to 7 days at approximately 23° C.
Root description: Thin root growing downward reaching as deep as 3 feet or deeper with sandy soil.

PLANT

General growth habit: Creeping, creating a dense mat.
Age of plant described: 90 days from rooted cutting in late summer.
Height: 2 cm.
Plant spread: Diameter is 160 cm in 90 days from rooted cutting planted in June 2024.
Growth rate: Vigorous.
Branching characteristics: Dense and prolific branching.
Length of primary lateral branches: 30 to 70 cm during the warm season at 3 months of age from rooted cuttings.
Diameter of lateral branches: 4 mm.
Quantity of primary lateral branches per linear cm: The plant continuously forms branches, approximately 2 to 4 linear cm.
Characteristics of primary lateral branches:
*Form*,—Round.
*Diameter*.—4 mm.
*Color*.—RHS Greyed-Orange 177B.
*Texture*.—Slightly scaly.
*Strength*.—Very strong, difficult to break.
*Internode length*.—Average 2.6 cm.

FOLIAGE

Leaf:
*Arrangement*.—Opposite.
*Quantity*.—Indefinite per branch.
*Average length*.—1.7 cm.
*Average width*.—0.9 cm.
*Shape of blade*.—Obovate.
*Apex*.—Broad Acute.
*Base*.—Attenuate.
*Margin*.—Serrate.
*Texture of top surface*.—Glabrous.
*Texture of bottom surface*.—Glabrous.
*Pubescence*.—None.
*Aspect*.—Nearly flat.
*Color*.—Young foliage upper side (front): RHS Green 137B. Young foliage under side (back): RHS Green 137C. Mature foliage upper side (front): RHS Green 137B. Mature foliage under side (back): RHS Green 137C.
*Venation*.—Type: Pinnate. Venation color upper side: RHS 137D. Venation color under side: RHS 137D.
*Petiole*.—Leaves sessile.

FLOWER

Natural flowering season: May to September.
Days to flowering from rooted cutting: 1-2 months, depending on temperature and light conditions.
Inflorescence and flower type and habit: Terminal umbel.
Rate of flower opening: 5 to 7 days from bud to fully opened flower.
Flower longevity on plant: About 13 days.
Persistent or self-cleaning: Persistent.
Bud:
*Shape*.—Oval.
*Length*.—0.6 cm.
*Diameter*.—0.4 cm.
*Color*.—RHS Purple 79D.
Inflorescence:
*Height/depth*.—0.8 cm.
*Diameter*.—1.0 cm.
*Average quantity of individual flowers per inflorescence*.—61.
Corolla:
Individual flower:
*Height/depth*.—0.6 cm.
*Diameter*.—0.4 cm.
Petals/lobes:
*Number*.—1 fully formed petal.
*Length*.—0.5 cm.
*Width*.—0.3 cm.

*Shape*.—Tube, flaring open at very end.
*Apex*.—Blunt round.
*Base*.—Fused.
*Margin*.—Entire. Ruffled at apex.
*Texture*.—Glabrous all surfaces.
*Color*.—When opening: Upper surface: RHS White N155C. Lower surface: RHS White N155C. Fully opened: Upper surface: RHS Purple 75B. Lower surface: RHS Purple 75B.

Throat:
*Color*.—Nearly RHS Yellow 14C.
*Texture*.—Glabrous.

Tube:
*Interior tube color*.—RHS 14C.
*Exterior tube color*.—RHS 14D.
*Texture*.—Glabrous.

Calyx:
*Form*.—Fused into a tube.
*Length*.—0.3 cm.
*Diameter*.—0.2 cm.
*Texture*.—Glabrous.
*Color*.—Upper surface: Near RHS Green 137D. Lower surface: Nearly RHS Green 137D.

Fragrance: None.

Pedicels: Not present.

Peduncles:
*Length*.—4 cm.
*Diameter*.—0.1 cm.
*Color*.—Yellow-Green 144B.
*Texture*.—Glabrous.

REPRODUCTIVE ORGANS

Stamens:
*Number* (*per flower*).—4.
*Filament length*.—0.05 cm.
*Anthers*.—Shape: Linear. Length: 0.05 cm. Color: Nearly RHS Yellow 14C.
*Pollen*.—Scant. Colored RHS Yellow 14C.

Pistils:
*Quantity per flower*.—1. Minute, not measurable.

OTHER CHARACTERISTICS

Seeds and fruits: Plants are sterile.

Disease/pest resistance/tolerance/susceptibility: Excellent resistance to common disease of *Lippia nodiflora*. New variety has improved resistance to disease under humid and hot conditions than parents. The most common pathogens found in *Lippia* are fungus including Southern Blight. No particular pest resistance observed.

Temperature tolerance: 'ECOLOPIA 4' has shown excellent resistance to high and low temperature extremes, having been grown successfully under temperature conditions ranging from a gentle frost outdoors, just below 0 degree Celsius, to 50 degree Celsius in a greenhouse without climate control.

Drought tolerance: 'ECOLOPIA 4' has excellent drought tolerance as set forth in WUCOLS IV regarding *Lippia* plants.

Physical durability: New variety has excellent tolerance to foot traffic.

Soil pH range: New variety has excellent tolerance to a range of soil pH from 4.0-12.0.

Pollinator or host plant information: The new variety hosts bees and other pollinator insects due to long blossom seasons. Not a provider of nectar to pollinator insects.

What is claimed is:

1. A new and distinct cultivar of *Lippia* plant named 'ECOLOPIA 4' as herein illustrated and described.

* * * * *